US012605172B2

(12) United States Patent
Kubacki et al.

(10) Patent No.: US 12,605,172 B2
(45) Date of Patent: Apr. 21, 2026

(54) METHODS AND SYSTEM FOR EXTRAMEDULLARY GUIDANCE

(71) Applicant: WRIGHT MEDICAL TECHNOLOGY, INC., Memphis, TN (US)

(72) Inventors: Meghan R. Kubacki, Cookeville, TN (US); Kian-Ming Wong, Lakeland, TN (US); Steven L. Haddad, Glenview, IL (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 529 days.

(21) Appl. No.: 18/175,578

(22) Filed: Feb. 28, 2023

(65) Prior Publication Data

US 2023/0346395 A1 Nov. 2, 2023

Related U.S. Application Data

(60) Provisional application No. 63/363,653, filed on Apr. 27, 2022.

(51) Int. Cl.
*A61B 17/17* (2006.01)
*A61F 2/46* (2006.01)
*A61B 17/56* (2006.01)

(52) U.S. Cl.
CPC ........ *A61B 17/1775* (2016.11); *A61F 2/4606* (2013.01); *A61B 2017/564* (2013.01)

(58) Field of Classification Search
CPC . A61B 17/1775; A61B 17/1682; A61B 17/17; A61B 17/16
See application file for complete search history.

(56) References Cited

U.S. PATENT DOCUMENTS

| | | | |
|---|---|---|---|
| 3,839,742 A | 10/1974 | Link | |
| 3,872,519 A | 3/1975 | Giannestras et al. | |

(Continued)

FOREIGN PATENT DOCUMENTS

| | | |
|---|---|---|
| CA | 2836651 | 3/2016 |
| CN | 101790353 | 7/2010 |

(Continued)

OTHER PUBLICATIONS

Search report issued for European patent application No. 13198280 dated Feb. 5, 2014.

(Continued)

*Primary Examiner* — Matthew J Lawson
(74) *Attorney, Agent, or Firm* — DUANE MORRIS LLP

(57) ABSTRACT

A system and method fare provided for preparing the distal tibia in an ankle replacement via an extra-medullary jig. An extra-medullary jig or C-bracket is positioned on the tibia with a registration reference and positioned with respect to a resection in the distal tibia via an anterior mounting block which is independent of the surface of the tibia. The mounting block allows the adjustment of the stem cartridge with respect to the registration reference such that the stem cartridge is properly aligned within the resection. The C-bracket is further attached to the tibia via an adjustable proximal alignment arm which attaches to a pin embedded in the proximal tibia. The C-bracket aligns the tibia, foot and ankle and the trajectory of the reamer, and is universal with respect to the left and right ankle.

11 Claims, 11 Drawing Sheets

(56)  References Cited

U.S. PATENT DOCUMENTS

| | | | |
|---|---|---|---|
| 3,886,599 A | 6/1975 | Schlein | |
| 3,889,300 A | 6/1975 | Smith | |
| 3,896,502 A | 7/1975 | Lennox | |
| 3,896,503 A | 7/1975 | Freeman et al. | |
| 3,975,778 A | 8/1976 | Newton, III | |
| 3,987,500 A | 10/1976 | Schlein | |
| 4,021,864 A | 5/1977 | Waugh | |
| 4,069,518 A | 1/1978 | Groth, Jr. et al. | |
| 4,156,944 A | 6/1979 | Schreiber et al. | |
| 4,166,292 A | 9/1979 | Bokros | |
| 4,204,284 A | 5/1980 | Koeneman | |
| 4,232,404 A | 11/1980 | Samuelson et al. | |
| 4,309,778 A | 1/1982 | Buechel et al. | |
| 4,470,158 A | 9/1984 | Pappas et al. | |
| 4,755,185 A | 7/1988 | Tarr | |
| 4,968,316 A | 11/1990 | Hergenroeder | |
| 5,041,139 A | 8/1991 | Brånemark | |
| 5,312,412 A | 5/1994 | Whipple | |
| 5,326,365 A | 7/1994 | Alvine | |
| 5,354,300 A | 10/1994 | Goble et al. | |
| 5,395,188 A | 3/1995 | Bailey et al. | |
| 5,423,825 A | 6/1995 | Levine | |
| 5,476,466 A | 12/1995 | Barrette et al. | |
| 5,601,563 A | 2/1997 | Burke et al. | |
| 5,628,749 A | 5/1997 | Vendrely et al. | |
| 5,634,927 A | 6/1997 | Houston et al. | |
| 5,667,511 A | 9/1997 | Vendrely et al. | |
| 5,674,223 A | 10/1997 | Cipolletti et al. | |
| 5,735,904 A | 4/1998 | Pappas | |
| 5,766,259 A | 6/1998 | Sammarco | |
| 5,768,134 A | 6/1998 | Swaelens et al. | |
| 5,776,200 A | 7/1998 | Johnson et al. | |
| 5,817,097 A | 10/1998 | Howard et al. | |
| 5,824,106 A | 10/1998 | Fournal | |
| 5,879,389 A | 3/1999 | Koshino | |
| 5,885,299 A | 3/1999 | Winslow et al. | |
| 5,888,203 A | 3/1999 | Goldberg | |
| 5,897,559 A | 4/1999 | Masini | |
| 5,935,132 A | 8/1999 | Bettuchi et al. | |
| 6,002,859 A | 12/1999 | DiGioia, III et al. | |
| 6,033,405 A | 3/2000 | Winslow et al. | |
| 6,053,922 A | 4/2000 | Krause et al. | |
| 6,102,952 A | 8/2000 | Koshino | |
| 6,183,519 B1 | 2/2001 | Bonnin et al. | |
| 6,245,109 B1 | 6/2001 | Mendes et al. | |
| 6,328,737 B1 * | 12/2001 | Moorcroft | A61B 17/66 |
| | | | 606/57 |
| 6,342,056 B1 | 1/2002 | Mac-Thiong et al. | |
| 6,344,043 B1 | 2/2002 | Pappas | |
| 6,409,767 B1 | 6/2002 | Pericé et al. | |
| 6,436,146 B1 | 8/2002 | Hassler et al. | |
| 6,478,800 B1 | 11/2002 | Fraser et al. | |
| 6,520,964 B2 | 2/2003 | Tallarida et al. | |
| 6,530,930 B1 | 3/2003 | Marino et al. | |
| 6,602,259 B1 | 8/2003 | Masini | |
| 6,610,067 B2 | 8/2003 | Tallarida et al. | |
| 6,610,095 B1 | 8/2003 | Pope et al. | |
| 6,620,168 B1 | 9/2003 | Lombardo et al. | |
| 6,645,215 B1 | 11/2003 | McGovern et al. | |
| 6,663,669 B1 | 12/2003 | Reiley | |
| 6,673,116 B2 | 1/2004 | Reiley | |
| 6,679,917 B2 | 1/2004 | Ek | |
| 6,719,799 B1 | 4/2004 | Kropf | |
| 6,824,567 B2 | 11/2004 | Tornier et al. | |
| 6,852,130 B2 | 2/2005 | Keller et al. | |
| 6,860,902 B2 | 3/2005 | Reiley | |
| 6,863,691 B2 | 3/2005 | Short et al. | |
| 6,875,222 B2 | 4/2005 | Long et al. | |
| 6,875,236 B2 | 4/2005 | Reiley | |
| 6,926,739 B1 | 8/2005 | O'Connor et al. | |
| 6,939,380 B2 | 9/2005 | Guzman | |
| 6,942,670 B2 | 9/2005 | Heldreth et al. | |
| 6,964,663 B2 | 11/2005 | Grant et al. | |
| 7,001,394 B2 | 2/2006 | Gundlapalli et al. | |
| 7,011,687 B2 | 3/2006 | Deffenbaugh et al. | |
| 7,025,790 B2 | 4/2006 | Parks et al. | |
| 7,163,541 B2 | 1/2007 | Ek | |
| 7,238,190 B2 | 7/2007 | Schon et al. | |
| 7,252,684 B2 | 8/2007 | Dearnaley | |
| 7,314,488 B2 | 1/2008 | Reiley | |
| 7,323,012 B1 | 1/2008 | Stone et al. | |
| 7,422,593 B2 * | 9/2008 | Cresina | A61B 17/66 |
| | | | 606/57 |
| 7,476,227 B2 | 1/2009 | Tornier et al. | |
| 7,481,814 B1 | 1/2009 | Metzger | |
| 7,485,147 B2 | 2/2009 | Papps et al. | |
| 7,534,246 B2 | 5/2009 | Reiley et al. | |
| 7,534,270 B2 | 5/2009 | Ball | |
| 7,615,082 B2 | 11/2009 | Naegerl et al. | |
| 7,618,421 B2 | 11/2009 | Axelson, Jr. et al. | |
| 7,625,409 B2 | 12/2009 | Saltzman et al. | |
| 7,641,697 B2 | 1/2010 | Reiley | |
| 7,678,151 B2 | 3/2010 | Ek | |
| 7,713,305 B2 | 5/2010 | Ek | |
| 7,717,920 B2 | 5/2010 | Reiley | |
| 7,749,224 B2 * | 7/2010 | Cresina | A61B 17/6491 |
| | | | 606/57 |
| 7,763,080 B2 | 7/2010 | Southworth | |
| 7,803,158 B2 | 9/2010 | Hayden | |
| 7,850,698 B2 | 12/2010 | Straszheim-Morley et al. | |
| 7,896,883 B2 | 3/2011 | Ek et al. | |
| 7,896,885 B2 | 3/2011 | Miniaci et al. | |
| 7,909,882 B2 | 3/2011 | Stinnette | |
| 7,914,533 B2 | 3/2011 | Nelson et al. | |
| 7,963,996 B2 | 6/2011 | Saltzman et al. | |
| 8,002,841 B2 | 8/2011 | Hasselman | |
| 8,012,217 B2 | 9/2011 | Strzepa et al. | |
| 8,034,114 B2 | 10/2011 | Reiley | |
| 8,034,115 B2 | 10/2011 | Reiley | |
| 8,048,164 B2 | 11/2011 | Reiley | |
| 8,110,006 B2 | 2/2012 | Reiley | |
| 8,114,091 B2 | 2/2012 | Ratron et al. | |
| 8,128,627 B2 | 3/2012 | Justin et al. | |
| 8,167,888 B2 | 5/2012 | Steffensmeier | |
| 8,172,850 B2 | 5/2012 | McMinn | |
| 8,177,841 B2 | 5/2012 | Ek | |
| 8,192,434 B2 * | 6/2012 | Huebner | A61B 17/60 |
| | | | 606/54 |
| 8,268,007 B2 | 9/2012 | Barsoum et al. | |
| 8,303,667 B2 | 11/2012 | Younger | |
| 8,313,492 B2 | 11/2012 | Wong et al. | |
| 8,317,797 B2 | 11/2012 | Rasmussen | |
| 8,323,346 B2 | 12/2012 | Tepic | |
| 8,337,503 B2 | 12/2012 | Lian | |
| 8,361,159 B2 | 1/2013 | Ek | |
| 8,366,559 B2 | 2/2013 | Papenfuss et al. | |
| 8,430,879 B2 | 4/2013 | Stoneburner et al. | |
| 8,475,463 B2 | 7/2013 | Lian | |
| 8,491,596 B2 | 7/2013 | Long et al. | |
| 8,579,980 B2 | 11/2013 | DeLurio et al. | |
| 8,715,362 B2 | 5/2014 | Reiley et al. | |
| 8,808,297 B2 | 8/2014 | Stemniski et al. | |
| 8,808,303 B2 | 8/2014 | Stemniski et al. | |
| 8,911,444 B2 | 12/2014 | Bailey | |
| 9,259,250 B2 | 2/2016 | Saravia et al. | |
| 9,480,571 B2 | 11/2016 | McGinley et al. | |
| 9,492,281 B2 | 11/2016 | Rouyer et al. | |
| 9,566,075 B2 | 2/2017 | Carroll et al. | |
| 9,629,726 B2 | 4/2017 | Reiley et al. | |
| 9,629,730 B2 | 4/2017 | Reiley | |
| 9,675,365 B2 | 6/2017 | Lancianese et al. | |
| 9,907,561 B2 * | 3/2018 | Luna | A61B 17/1682 |
| 10,034,678 B2 | 7/2018 | Park et al. | |
| 10,039,558 B2 | 8/2018 | Park et al. | |
| 10,111,674 B2 | 10/2018 | Crainich et al. | |
| 10,136,904 B2 | 11/2018 | McGinley et al. | |
| 10,149,687 B2 | 12/2018 | McGinley et al. | |
| 10,182,832 B1 | 1/2019 | Saltzman et al. | |
| 10,206,688 B2 | 2/2019 | Park et al. | |
| 10,213,309 B2 | 2/2019 | Lindsey et al. | |
| 10,743,999 B2 | 8/2020 | Reiley | |
| 10,940,012 B2 | 3/2021 | Sander et al. | |
| 11,013,520 B2 | 5/2021 | Gareiss et al. | |
| 11,246,610 B2 * | 2/2022 | Lee | A61F 2/4202 |

(56)  References Cited

U.S. PATENT DOCUMENTS

| | | |
|---|---|---|
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0193268 A1 | 9/2004 | Hazebrouck |
| 2004/0215204 A1* | 10/2004 | Davison ............. A61B 17/7225 |
| | | 606/98 |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2005/0267481 A1 | 12/2005 | Carl et al. |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0229730 A1 | 10/2006 | Reiley et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0042215 A1 | 2/2010 | Stalcup et al. |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0212138 A1 | 8/2010 | Carroll et al. |
| 2010/0241237 A1 | 9/2010 | Pappas |
| 2010/0256773 A1 | 10/2010 | Thijs et al. |
| 2010/0262150 A1 | 10/2010 | Lian |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0071645 A1 | 3/2011 | Bojarski et al. |

| | | |
|---|---|---|
| 2011/0106268 A1 | 5/2011 | Deffenbaugh et al. |
| 2011/0112542 A1 | 5/2011 | Gross |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0245835 A1 | 10/2011 | Dodd et al. |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053591 A1 | 3/2012 | Haines et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0130434 A1* | 5/2012 | Stemniski .......... A61B 17/1775 |
| | | 606/86 R |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271314 A1 | 10/2012 | Stemniski et al. |
| 2012/0271430 A1 | 10/2012 | Arnett et al. |
| 2012/0277745 A1* | 11/2012 | Lizee ................. A61B 17/1739 |
| | | 606/59 |
| 2013/0041473 A1 | 2/2013 | Rouyer et al. |
| 2013/0116797 A1 | 5/2013 | Coulange et al. |
| 2014/0020690 A1* | 1/2014 | Triplett ................. A61G 13/128 |
| | | 128/845 |
| 2014/0039565 A1 | 2/2014 | Martineau et al. |
| 2014/0163570 A1 | 6/2014 | Reynolds et al. |
| 2014/0236157 A1 | 8/2014 | Tochigi et al. |
| 2014/0276853 A1 | 9/2014 | Long et al. |
| 2014/0296995 A1 | 10/2014 | Reiley et al. |
| 2014/0309640 A1 | 10/2014 | Smith et al. |
| 2014/0336658 A1 | 11/2014 | Luna et al. |
| 2015/0045801 A1 | 2/2015 | Axelson et al. |
| 2015/0257900 A1 | 9/2015 | Dees, Jr. |
| 2015/0305791 A1* | 10/2015 | Purohit .............. A61B 17/8872 |
| | | 606/96 |
| 2016/0135815 A1 | 5/2016 | Loring et al. |
| 2016/0135857 A1 | 5/2016 | Marrero, Sr. |
| 2016/0256175 A1* | 9/2016 | Cummings ........ A61B 17/1703 |
| 2016/0361071 A1 | 12/2016 | Mahfouz |
| 2016/0367371 A1 | 12/2016 | De Beaubien et al. |
| 2017/0189198 A1 | 7/2017 | Reiley et al. |
| 2018/0177511 A1 | 6/2018 | Luna et al. |
| 2018/0177513 A1 | 6/2018 | Stemniski et al. |
| 2018/0242987 A1* | 8/2018 | Lintula .............. A61B 17/1725 |
| 2018/0263639 A1 | 9/2018 | McGinley et al. |
| 2019/0029700 A1* | 1/2019 | Free ................... A61B 17/1682 |
| 2019/0059917 A1 | 2/2019 | Saltzman |
| 2019/0059918 A1 | 2/2019 | Saltzman et al. |
| 2019/0076261 A1 | 3/2019 | Mutchler et al. |
| 2019/0133612 A1 | 5/2019 | McGinley |
| 2019/0150957 A1 | 5/2019 | Wilkinson |
| 2019/0350717 A1 | 11/2019 | Tuttle |
| 2020/0046374 A1 | 2/2020 | Luttrell et al. |
| 2020/0297353 A1 | 9/2020 | Bomar et al. |
| 2022/0192687 A1* | 6/2022 | Majors .............. A61B 17/7291 |
| 2022/0316504 A1 | 10/2022 | Kubacki |
| 2024/0050164 A1* | 2/2024 | Stemniski .......... A61B 17/1775 |

FOREIGN PATENT DOCUMENTS

| | | |
|---|---|---|
| EP | 2967697 | 4/2018 |
| EP | 3354233 | 10/2019 |
| GB | 2480846 | 12/2011 |
| JP | H11-500035 | 1/1999 |
| JP | 2006150055 | 6/2006 |

(56) References Cited

FOREIGN PATENT DOCUMENTS

| JP | 2007508123 | | 4/2007 |
|----|------------|----|--------|
| JP | 2007518453 | | 7/2007 |
| JP | 2007519477 | | 7/2007 |
| JP | 2007536011 | | 12/2007 |
| JP | 2009148597 | | 7/2009 |
| JP | 2011526189 | | 10/2011 |
| JP | 2012518517 | | 8/2012 |
| JP | 2013500810 | | 1/2013 |
| JP | 2013511358 | | 4/2013 |
| JP | 5412334 | | 2/2014 |
| JP | 2014131738 | | 7/2014 |
| WO | WO 9625106 | | 8/1996 |
| WO | WO 0166021 | A1 | 9/2001 |
| WO | WO 2005011523 | A2 | 2/2005 |
| WO | WO 2005037135 | | 4/2005 |
| WO | WO 2006022923 | | 3/2006 |
| WO | WO 2006023824 | | 3/2006 |
| WO | WO 2006099270 | | 9/2006 |
| WO | WO 2007084846 | | 7/2007 |
| WO | WO 2009143374 | | 11/2009 |
| WO | WO 2009158522 | | 12/2009 |
| WO | WO 2010099142 | | 9/2010 |
| WO | WO 2010135156 | | 11/2010 |
| WO | WO 2011015863 | | 2/2011 |
| WO | WO 2011063281 | | 5/2011 |
| WO | WO 2011151657 | | 12/2011 |
| WO | WO 2012088036 | | 6/2012 |
| WO | WO 2012116089 | | 8/2012 |
| WO | WO 2012158917 | | 11/2012 |
| WO | WO 2013169475 | | 11/2013 |
| WO | WO 2014152535 | | 9/2014 |
| WO | WO 2015167581 | | 11/2015 |
| WO | WO 2016005722 | | 1/2016 |
| WO | WO 2016039762 | | 3/2016 |
| WO | WO 2016181168 | | 11/2016 |

OTHER PUBLICATIONS

International Search Report for International patent application No. PCT/US2014/027448 dated Jul. 7, 2014.

International Preliminary Report on Patentability issued for International patent application No. PCT/US2014/027448, Sep. 15, 2015, 8 pages.

Partial European Search Report issued in connection with European patent application No. 14768333.8, Oct. 26, 2016, 6 pages.

Patent Examination Report No. 1 issued in connection with Australian patent application No. 2015202080, Jul. 5, 2016, 4 pages.

First Office Action issued for Japanese patent application No. 2016-117842, Sep. 12, 2017, 5 pages.

First Office Action issued in connection with corresponding Japanese Patent Application No. 2020-016447, Apr. 6, 2021, 4 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

First Office Action in corresponding Canadian Patent Application No. 2,904,652, Jan. 28, 2020, 5 pages.

Final Office Action issued in connection with corresponding Japanese Patent Application No. 206-502443, May 15, 2018, 3 pages.

Extended European Search Report issued in connection with corresponding European Patent Application No. 18160378.8, Jun. 29, 2018, 7 pages.

Second Office Action issued in connection with corresponding Chinese Patent Application No. 2018071101785100, dated Jul. 16, 2016, 6 pages.

First Office Action in corresponding Japanese Patent Application No. 2018-178853, Sep. 3, 2018, 3 pages.

Examination Report No. 1 issued in connection with corresponding Australian Patent Application No. 20182000073, Dec. 24, 2018, 3 pages.

First Office Action issued in connection with corresponding Japanese Patent Application No. 2018-092289, Mar. 5, 2019, 2 pages.

Extended European Search Report and Opinion in connection with European Patent Application No. 14768333.8, dated Jan. 30, 2017, 10 pages.

First Office Action issued in connection with Chinese Patent Application No. 2017800899442 dated Apr. 6, 2022, 8 pages.

International Search Report and Written Opinion issued in connection with International Patent Application No. PCT/US2021/025873, Sep. 2, 2021.

Orthopedic Designs North America, Inc., http://odi-na.com/?service=talon-distalfix-fermoral-nail-system, accessed via Internet, Jul. 22, 2022.

Arthrex, "Arthrex—Intramedullary Nails," https://ww.arthrex.com/foot-ankle/intramedullary-nails, accessed via Internet, Jul. 22, 2022.

Inbone II Total Ankle Surgical Technique, Wright Medical Technology, Inc., Mar. 12, 2014, 64 pages.

Infinity Total Ankle System Surgical Technique, Wright Medical Techology, Inc., Aug. 8, 2015, 76 pages.

First Examination Report issued in connection with Australian Patent Application No. 2020277219, Nov. 19, 2021, 7 pages.

International Search Report and Written Opinion issued in connection with International Patent Application No. PCT/US2016/023729, Feb. 14, 2017, 14 pages.

First Examination Report issued in connection with Australian Patent Application No. 2019246766, Apr. 17, 2020, 9 pages.

Supplementary European Search Report issued in connection with corresponding European Patent Application No. 16895669.6 Oct. 21, 2019, 6 pages.

Office Action in connection with corresponding Canadian Patent Application No. 3,014,284, Jun. 17, 2019, 4 pages.

First Examination issued in connection with Australian Patent Application No. 2016398429, Jan. 21, 2019, 4 pages.

International Search Report and Written Opinion issued in connection with International Patent Application No. PCT/US2021/071308, Dec. 27, 2021, 10 pages.

Extended European Search Report issued in connection with European Patent Application No. 22185245.2, Nov. 28, 2022, 9 pages.

International Search Report and Written Opinion issued in connection with International Patent Application No. PCT/US2021/057014, Mar. 17, 2022, 19 pages.

* cited by examiner

SECTION A - A

METHODS AND SYSTEM FOR EXTRAMEDULLARY GUIDANCE

CROSS-REFERENCE TO RELATED APPLICATION

This application claims priority under 35 U.S.C. § 119(e) to U.S. Provisional Application No. 63/363,653, filed on Apr. 27, 2022, the entire contents of which are incorporated herein by reference.

TECHNICAL FIELD

The disclosed subject matter relates generally to a physical guide and jig to assist an orthopedic surgeon performing intramedullary boring of the tibia during ankle replacement.

BACKGROUND

Total joint replacement prostheses typically include a specially designed jig or fixture to enable a surgeon to make accurate and precise bone resections, and bores in and around the joint being prepared to accept the prosthesis. The ultimate goal with any total joint prosthesis is to restore the function and structure of the natural, healthy structures that the prosthesis is replacing. Should the prosthesis not be properly implanted to the joint, i.e., an ankle or knee, the misalignment could result in discomfort to the patient, gait problems, or degradation of the prosthesis. Guides or jigs to stabilize the position of bones and guide surgical instruments have been commonly used in full or partial ankle joint replacements. Several prior art system and methods exist for performing these replacements, one such prior art system uses a large rigid foot holder in which the foot and leg of the patient is rigidly constrained in the foot holder where the joint space between tibia and the talus is cut and the inter-medullary is reamed. Each of these procedures conducted with reference to the rigid foot holder. For example, both an anterior fixture guide and saw guide as well as the guide for drilling a primary hole are referenced to the jig. In these prior art systems, the positioning of the foot on the jig generally requires the movement of the foot and not the jig and associated guides. FIG. 1 illustrates one such prior art jig 140, as may be seen from the figure, the jig is large, rigid and is secured to the table 145 or other support. The jig 140 includes a foot plate 142 stabilizing the foot and a calf tray 141 stabilizing the lower leg 110. The leg 100 is also secured to the jig 140 via a pin in the calcaneus 113. The lower leg 110 is positioned with respect to the jib via alignment rods 147 fixed on the jig 140 via fluoroscopy such that the tibia 111 and talus 112 may be properly aligned for reaming. Both the form shaping and the reaming are preformed while the lower leg is positioned within the jig 140 and again with reference to the jig 140.

Today a simplistic, light, surgeon manipulatable, left and right foot interchangeable extra-medullary jig system does not exist to accurately and efficiently implant an intramedullary total ankle prosthesis. However, it is desirable to design such a system that combines features of the tabletop complex jig and rigid foot holder with a streamlined, amenable extra-medullary jig to create an optimal construction that allows the surgeon to simply position the jig with respect the patient while maintaining the proper alignment and positioning for the intra-medullary reaming required in a full ankle replacement.

The disclosed subject matter utilizes fixation features in the calcaneus, distal tibia, and proximal tibia, as well as a joint space filling device to maintain a rigid construct for preparing the intramedullary canal. The disclosed subject matter uses the simplified C-bracket design and features and combines them with some of the rigid fixation features from the foot holder. These features in conjunction with a proximal, adjustable fixation unit create an easy-to-use extramedullary jig to prepare an intramedullary implant. The disclosed subject matter additionally features heel cups for calcaneal fixation, forefoot blocks for foot stabilization, a proximal fixation unit for jig rigidity, and non-patient specific joint space filling devices for jig rigidity.

SUMMARY

The embodiments described herein are directed to a system, apparatus and method for reaming the tibia medullary canal with an external guide. In addition to or instead of the advantages presented herein, persons of ordinary skill in the art would recognize and appreciate other advantages as well.

In embodiments, a system for ankle replacement is presented which includes a C-bracket and a registration reference. The C-bracket including two parallel rails extending longitudinal and connected at a proximal end by a proximal end brace and at a distal end by a distal end brace, each the proximal and distal end braces extending perpendicular between the two parallel rails. The C-bracket further includes first and second cross members extending between the two parallel rails and fixable to a plurality of longitudinal positions along the rails. A distal alignment arm extends from the first cross member, perpendicular to both the first cross member and the two parallel rails and a proximal alignment arm extends from the second cross member, the proximal alignment arm having a mount for fixing an alignment pin at one of a plurality of orientations. The C-bracket further includes a foot bracket extending from the distal end of the parallel rails which is perpendicular to the plane defined by the rails. The registration reference includes one or more pins and pin sleeves which engage the pins and may also include a registration housing which receives the pin sleeves and is adjustable vertically with respect to the pin sleeves. The system further may include an anterior mounting block and stem cartridge, the anterior mounting block connecting to the distal alignment arm and registers the C-bracket to the registration reference.

In some embodiments, a method for preparing the distal tibia in an ankle replacement via an extra-medullary jig is presented. The method including positioning a registration reference mounting a stem cartridge to the mounting block; attaching an anterior mounting block to the tibia with respect to the registration reference; and aligning the anterior mounting block such that the stem cartridge is properly position with respect to the tibia resection. The method further includes positioning the extra-medullary jig (i.e. C-bracket) with respect to the foot and leg associated with the ankle via the anterior mounting block; attaching the proximal alignment arm extending from the extra-medullary jig to the tibia via an alignment pin fixed in the tibia; and, reaming the tibia medullary canal utilizing the extra-medullary jig.

In yet other embodiments, a fixed reference for registering medullary reaming guide with joint space cutting is presented. The reference including a reference housing, a plurality of pin sleeves; each of the pin sleeves configured to fit over each of a plurality of reference pins set in a bone. The reference housing defining a plurality of cavities, each of the cavities defining a geometric shape corresponding to a cross section of the plurality of pin sleeves, so as to allow each of the plurality of cavities to receive a respective one of the plurality of pin sleeves; and, wherein the reference housing further including a set screw to selectively fix the reference housing at a plurality of locations along the pin sleeves.

In still other embodiments, an adjustable registration system for positioning a C-channel guide with respect to a fixed reference is presented. The registration system including a registration block and a registrations reference. The registration block including an attachment feature configured to attached to a distal alignment arm, an attachment feature to configured to accept a stem cartridge and a registration reference pocket configured to fix the registration reference within via a set screw. The registration reference including a reference housing, a plurality of pin sleeves configured to fit over each of a plurality of reference pins set in the tibia. The reference housing defining a plurality of cavities having a geometric shape corresponding to a cross section of the plurality of pin sleeves, so as to allow each of the cavities to receive a respective one of the plurality of pin sleeves; and, another set screw to configured to selectively fix the reference housing along the pin sleeves.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 1:
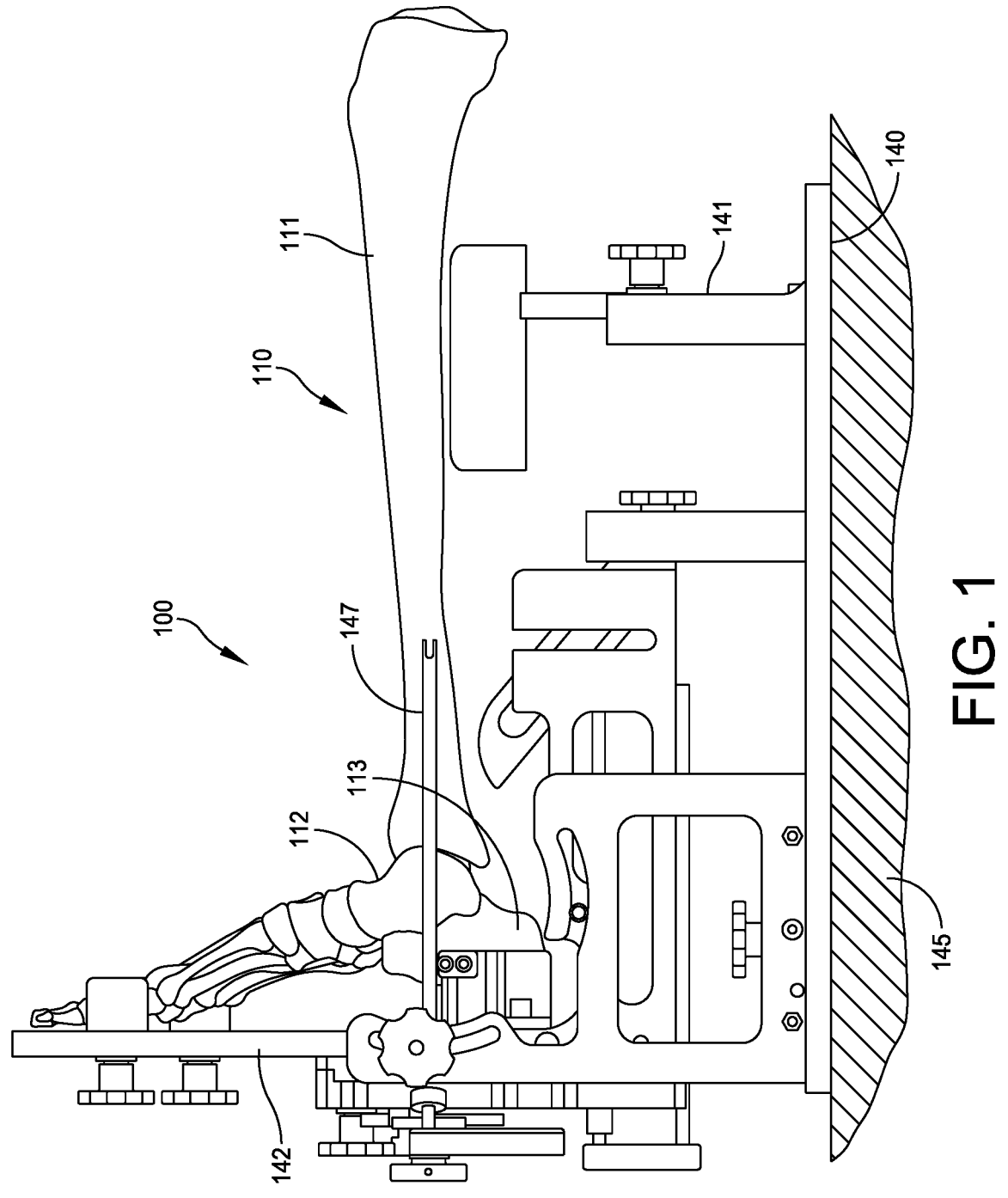
FIG. 1 is an illustration of a prior art table top guide fixture for total ankle replacements.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, or otherwise, such that the connection allows the pertinent devices or components to operate with each other as intended by virtue of that relationship.

Figure 2:
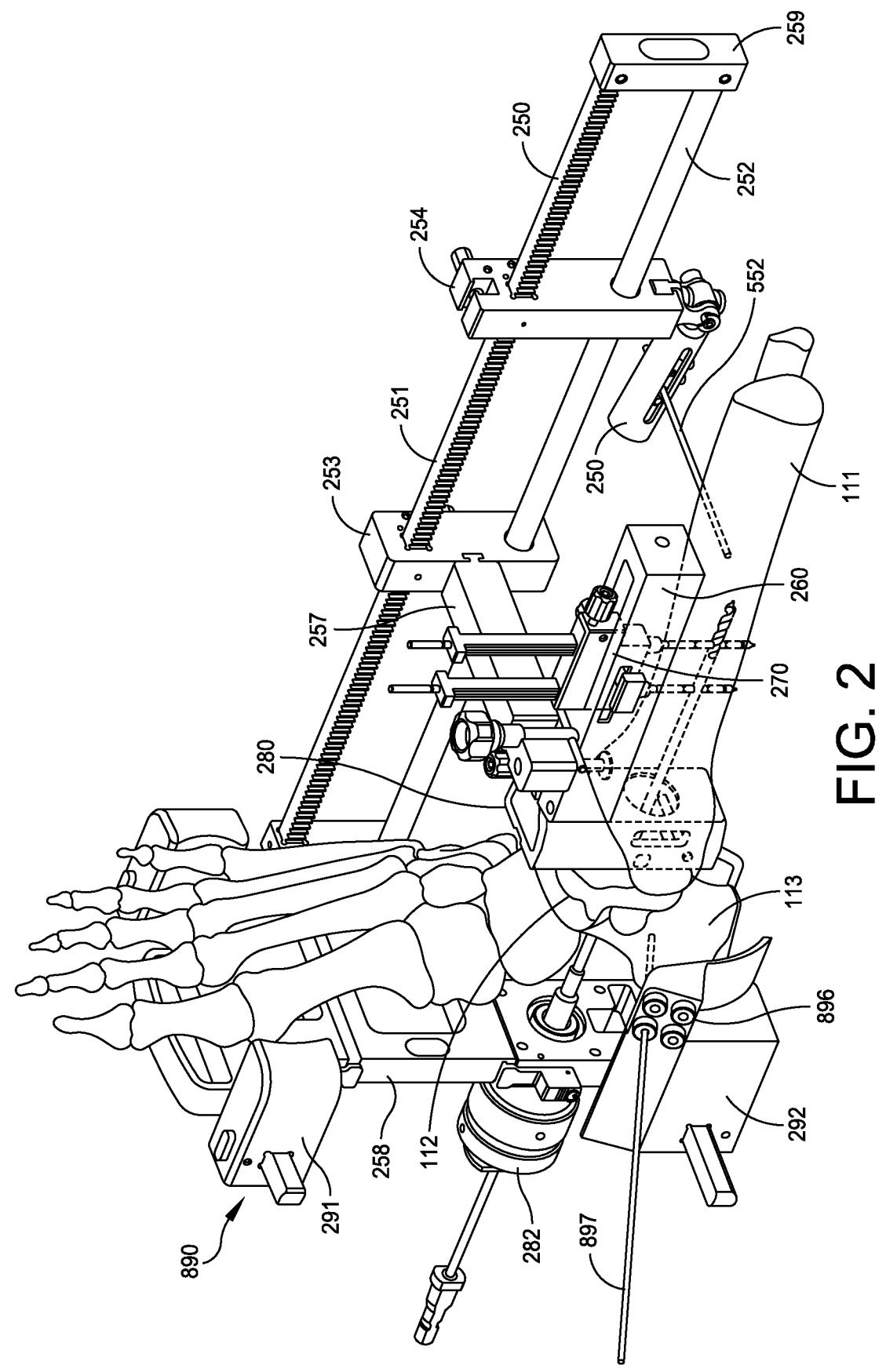
FIG. 2 is an illustration of extra-medullary jig in accordance with embodiments of the disclosed subject matter.

Turning to the drawings, FIG. 2 shows an extra-medullary jig system according to embodiments of the disclosed subject matter. Embodiments of the extra-medullary jig system as described herein includes a C-bracket assembly 250 (described in detail with respect to FIG. 4), an anterior mounting block 260 (described in detail with respect to FIG. 3), a registration reference 270 (described in detail with respect to FIG. 7A), a stem cartridge 280, a foot pad assembly 890 (described in detail with respect to FIG. 8) and a bushing 282

The anterior mounting block 260 connects to the C-bracket assembly 250 via a distal alignment arm 257. The anterior mounting block 260 attaches to the tibia 111 via the registration reference 270. The stem cartridge 280 also is connected to the anterior mounting block 260. The C-bracket assembly 250 is also affixed to the tibia 111 via the proximal alignment arm 256 and pin 552. The attachment to the tibia 111 via the proximal alignment arm 256 and pin is not location specific but serves to stabilize the C-bracket assembly 250 with respect to the lower leg 110. The foot pad 290 further serves to secure the lower leg 110 with respect to the C-bracket assembly 250. The foot pad 890 includes a forefoot assembly 291 and a heel cup assembly 292.

Figure 3:
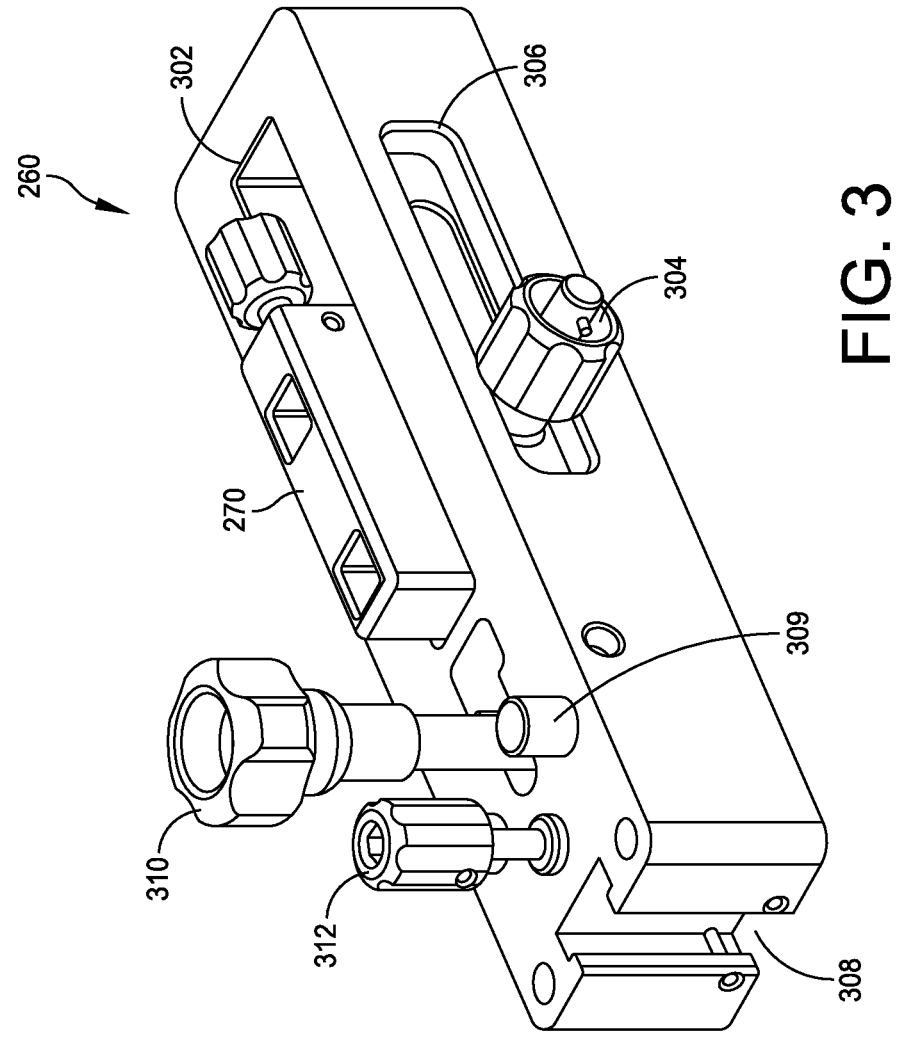
FIG. 3 is an illustration of an anterior mounting block in accordance with embodiments of the disclosed subject matter.
Figure 10A:
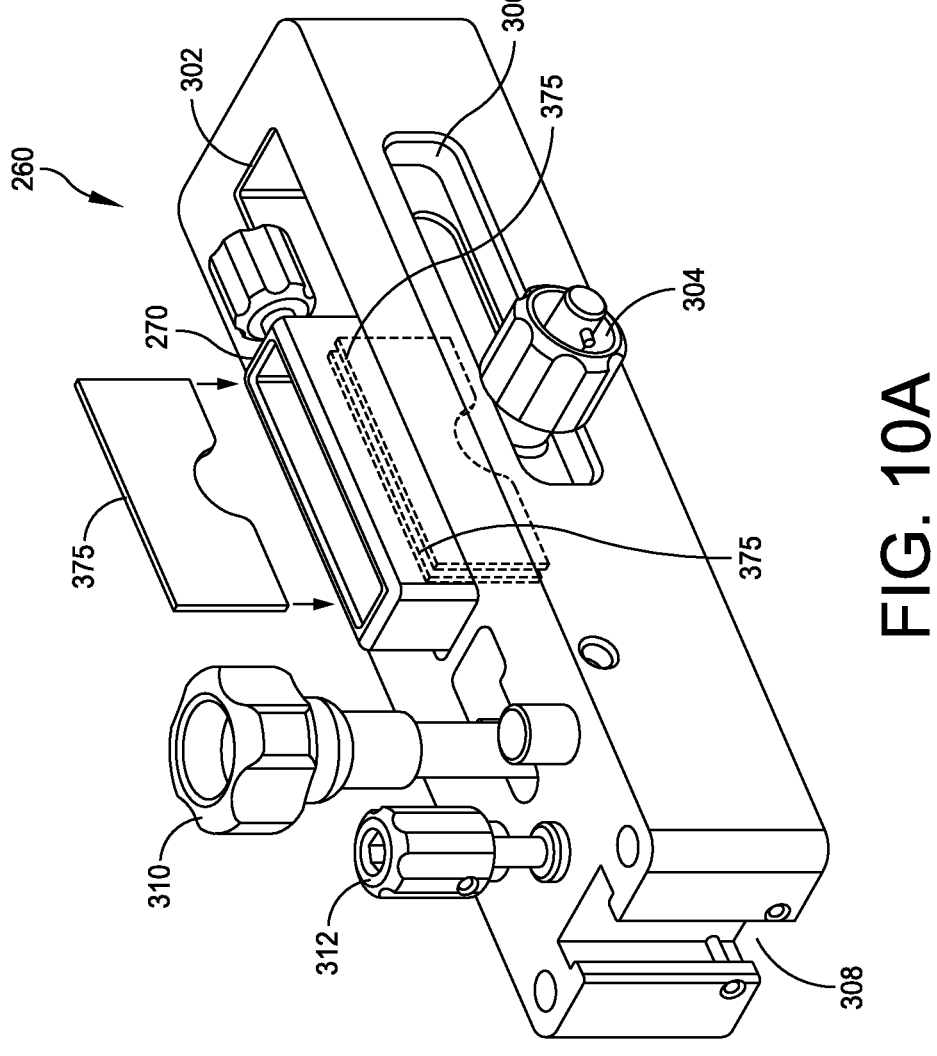
Figure 10B:
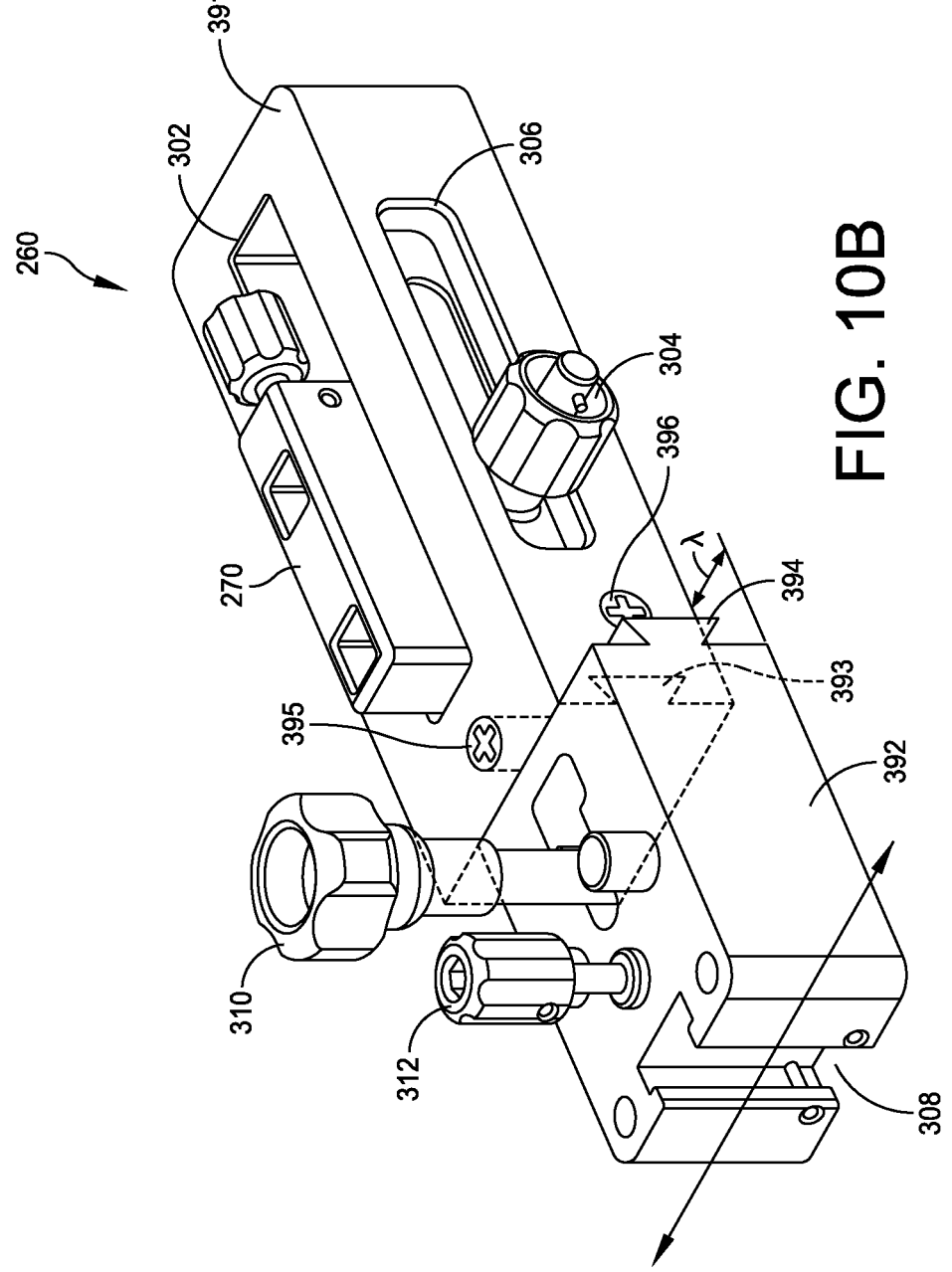

FIG. 3 is an illustration of an anterior mounting block 260. As described earlier the anterior mounting block 260 attaches the C-bracket assembly 250 to the tibia via the registration reference 270. The anterior mounting block 260 defines a rectangular cavity 302 to receive the registration reference 270. The cavity 302 is sized to allow the adjustment of the registration reference 270 along the longitudinal axis parallel to the sagittal plane, and may further allow for lateral adjustment of the anterior mounting block 260 with respect to the registration reference 270. The registration reference 270 is fixed with respect to the anterior mounting block in the lateral axis and the anteroposterior axis, via the cavity walls, adjustment screws and/or the compression slot 306 respectively. Adjustment of the position of the anterior mounting block 260 with respect to the registration reference anti-parallel to the sagittal plane may be accomplished by adjustment screws or shims as shown in FIG. 10A. The registration reference 270 is adjustably fixed in the cavity 302 along the longitudinal axis by the interaction of a compression slide lock 304 with the compression slot 306. Alternatively, the anterior mounting block 260 may be formed in two parts such that the proximal portion 391 may be adjusted laterally with respect to the distal portion 392 of the anterior mounting block 260 as shown in FIG. 10B. Another alternative to allow lateral adjustment may be accomplished via the attachment of the stem cartridge 280.

FIGS. 10A and 10B illustrate the lateral adjustment of the anterior mounting block 260 with respect to the registration reference 270, such that the stem cartridge 280 is properly aligned with the tibia resection. As shown in FIG. 10A, a plurality of shims or wedges 375 may be used to adjust the lateral positioning of the anterior mounting block 260. Once the lateral position is set with the insertion of the shims 375, the compression slide lock 304 may be tightened thereby fixing the both the longitudinal positioning and lateral positioning of the anterior mounting block 260 on the tibia 111. The anterior mounting block 260 may also be formed of two portions, a proximal portion 391 and a distal portion 392. As shown in FIG. 10B, the distal portion 392, upon which the stem cartridge 280 attaches, may be adjusted laterally by an offset λ with respect to the proximal portion 391. As shown the distal portion 392 includes a rail 394 which cooperates with a channel 393 in the proximal portion 391. The position of the distal portion 392 may be fixed with set screw 395, or worm screw 396. Other methods/mechanisms as known in the art that allow for lateral adjustment between the portions are also envisioned.

The anterior mounting block 260 is attached to the distal alignment arm 257 via a compression screw 310 and positioning dowels 309. In attaching the C-bracket assembly 250, the distal alignment arm 257 is positioned such that positioning dowels 309 are received in cooperating bores 652 (see FIG. 6). The compression screw 310 is then swung from a longitudinal orientation to an upright position within a cooperating slot 653 in the distal alignment arm 257, the compression screw 310 is then tightened thus securing the anterior mounting block 260 to the C-bracket assembly 250 via the distal alignment art 257. The attachment between the anterior mounting block 260 and the distal alignment arm 257 creates a rigid attachment fixing each with respect to the other in all three dimensions. The anterior mounting block 260 may further include a channel (groove) 308 aligned generally parallel to the anteroposterior axis for receiving a cooperating track (tongue) of the stem cartridge 280. A compression screw 312 extends through the anterior mounting block 260 to assist in positioning the stem cartridge with respect to the anterior mounting block 260 in the AP plane. Other arrangements for attaching the stem cartridge to the anterior mounting block 260 are also envisioned.

Figure 4:
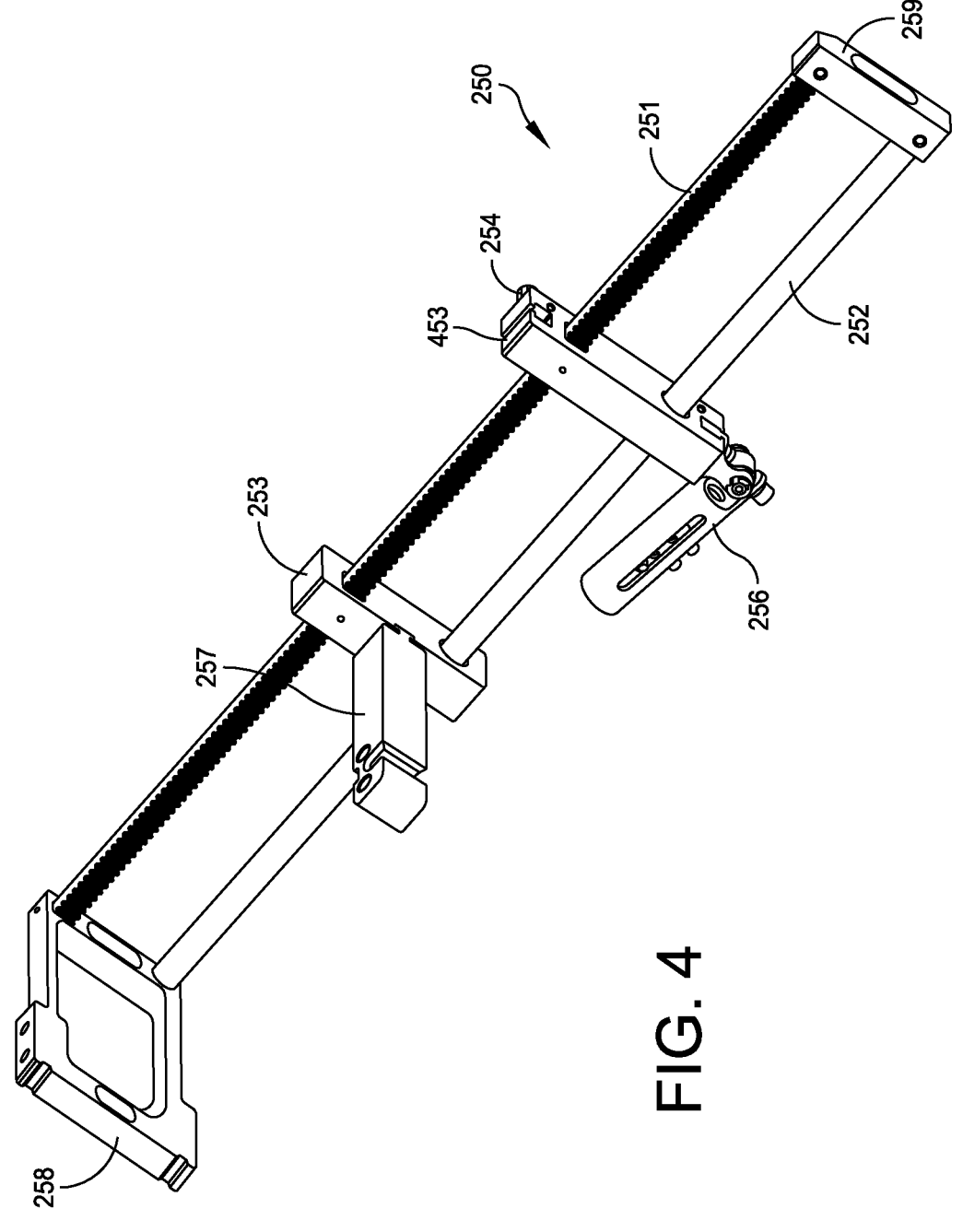
FIG. 4 is an illustration of a C-bracket in accordance with embodiments of the disclosed subject matter.

Turning to FIG. 4, in addition to the proximal and distal alignment arms 256 and 257, the C-bracket assembly 250 includes parallel rails 251 and 252, connected together via respective distal and proximal end braces 258, 259. A distal cross member 253 extends between the two parallel rails and is positional to any of the longitudinal positions established by teeth on the upper or lower rails, alternatively, the rails may be smooth and the position of the cross members may be established by frictional or interference engagement with the rails. In some embodiments, the distal cross member 253 ratchets (e.g. clicks) into position over on the upper rail 251 and then is secured by a set screw or clamp (not shown) on the lower rail 252. Similarly, a proximal cross member 254 extends between the two parallel rails and is positional to any of the longitudinal positions established by teeth on the upper or lower rails. The proximal cross member also ratchets into the desire position over on the upper rail 251 and then is secured by a set screw to the lower rail 252. Other positioning and fixing schemes are also envisioned and thus embodiments of the disclosure subject matter are not limited to only those shown. As shown in the embodiment of FIG. 4, the toothed rail 251 is a bar, with the lower rail 252 being a rod, however other geometries/configurations for the rails are also envisioned, and the rail embodiments shown should not be considered limiting the scope of the disclosed subject matter. The C-Bracket 250 may be constructed of extruded Polyphenysulfone (Radel®), aluminum, carbon fiber, plastic and/or stainless steel as well as other materials having properties appropriate given the functions and uses of the C-Bracket 250.

Figure 5:
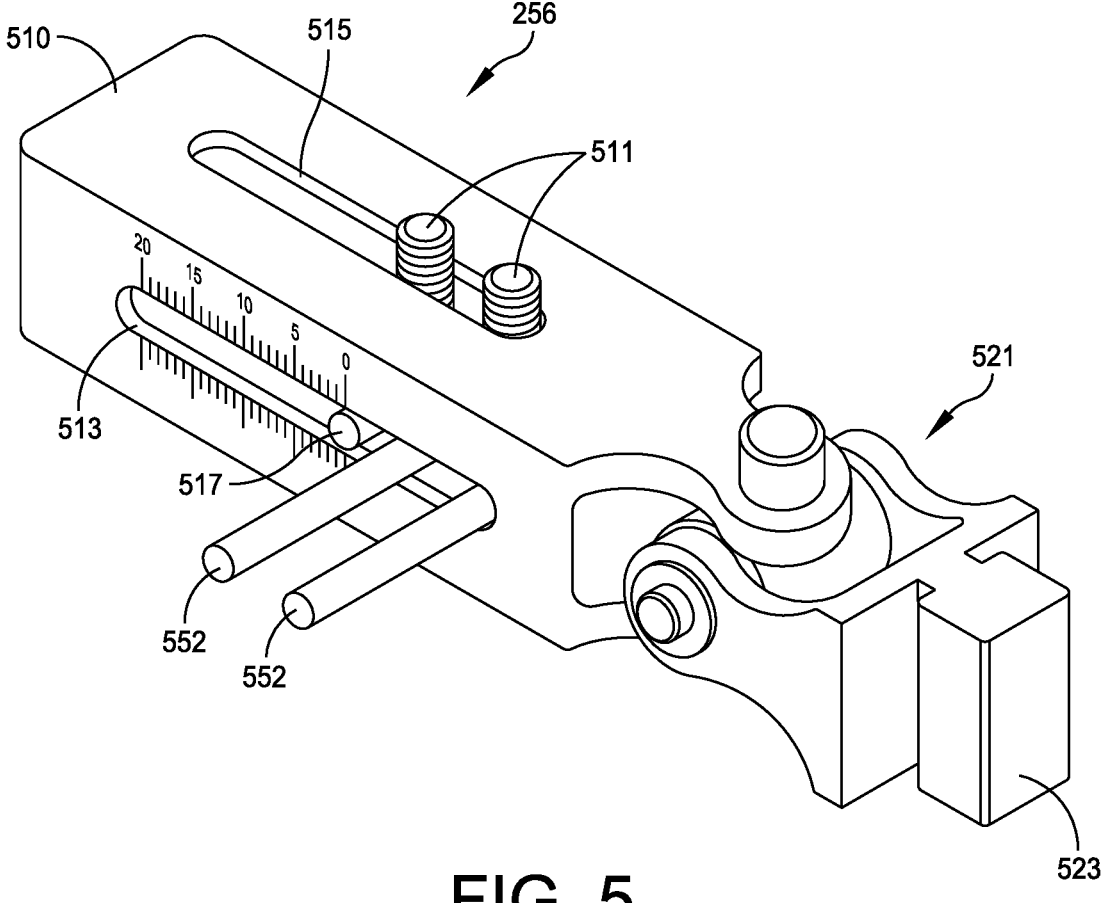
FIG. 5 is an illustration of a proximal alignment arm in accordance with embodiments of the disclosed subject matter.

The proximal alignment arm 256 extends from the proximal cross member 245 and allows for multiplaner fixation to the tibia 111 via pin 552. Both ends of the proximal cross member 245 include an attachment T-channel 453 by which the proximal alignment arm 256 may attach. This arrangement allows for the C-bracket to be used on either leg, or different sides of the same leg. For example, FIG. 2 illustrates the C-bracket assembly 250 on a right foot, and thus the proximal alignment arm 256 is positioned proximate to rail 252, if the C-bracket assembly were to be used on the left leg, the C-bracket assembly 250 would be flipped about the longitudinal axis and the proximal alignment arm 256 would be located on the other end of the proximal cross member 245 proximate rail 251. The proximal alignment arm 256 attaches the C-bracket assembly 250 to the tibia 111 via a pin(s) 552 (see FIGS. 2, 5). Unlike the distal alignment arm 257, the orientation of the proximal alignment arm 256 with respect to the cross member 254 is selectable. An embodiment of the proximal alignment arm 256 is shown in FIG. 5. Other attachment arrangements as will be apparent to those having skill in the art are also envisioned.

The distal end brace 258 extends perpendicular to the parallel rails and is adapted to receive a foot brace assembly 890. The foot brace assembly 890 is further described with respect to FIG. 8. The foot brace assembly 890 includes a fore foot assembly 881 and heel cup assembly 882. The foot brace assembly 890 attaches to the distal end brace 258 via dowels 895 (not shown for the heel cup assembly) and latches 893 and 894 to secure the position of the fore foot and heel assemblies. The foot brace assembly 890 includes left and right forefoot blocks 891a and 891b. The forefoot blocks 891a and 891b affix to a rail(s) 884 and are positional upon the rail 884 via a compression spring apparatus biased to fix the position of the block and allow movement of the forefoot blocks when the compression spring apparatus is depressed by the surgeon. Other positioning schemes are also envisioned. The fore foot blocks 891a and 891b may be specifically contoured with respect to either the right or left foot and/or the respective size of the patient's forefoot. The foot brace assembly 890 preferably includes a heel cup assembly 882 with two adjustable heel cups 892a and 892b and a bushing attachment 885 to position the drill shaft for reaming. The heel cups 892 are also adjustably along a ratcheted rail 883 and position the calcaneus with respect to the drill shaft. The heel cups 892 are also preferably contoured to generally approximate the heel shape. Additionally, the heel cups 892 may include a plurality of pin holes 896 (See FIG. 2) for fixing the orientation of pins (rods) 897 driven into the calcaneus, thus fixing the calcaneus with respect to the bracket 250 and the bushing 885.

FIG. 5 illustrates a proximal alignment arm 256. As noted above, the proximal alignment arm 256 extends from either end of cross member 254, depending upon which of the right or left ankle is being positioned within the bracket 250 or preference of the surgeon. The T-key 523 seats within the attachment T-channel 453. Again other attachment mechanisms such as dovetails, bayonet fittings, etc. as known in the art are also envisioned and the specific illustration of the T-channel and corresponding key are not intended to limit the scope of the disclosed subject matter. The proximal alignment arm 256 includes a universal joint 521 allowing multi axial positioning of the proximal alignment arm with respect to the bracket 250. The proximal arm 256 includes an elongated member 510 defining a set screw groove 515 and a pin groove 513. The set screw groove 515 allows access to the set screws 511 which sets the position of the pins 552 with in a pin carriage and with respect to the arm 256. Similarly the pin groove 513 allows the pin(s) 552 to be positioned along the groove 513. The groove 513 is indexed and the pin(s) 552 position is referenced by pointer 517 that travels with the pin(s) 552 in the pin carriage along the pin groove 513. The pin carriage, moves within the elongated member 510 and is fixed with respect to the elongated member 510 via a threaded bushing or set screw (not shown). In practice, the proximal alignment arm 256 allows the proximal end of the c-bracket 250 to be adjustably positioned in multiple directions with respect to the pin(s) 552. Once the position of the C-bracket 250 is established, the position of the pin(s) 552 with respect to pin groove 513 and longitudinally with respect to the proximal arm 256 is fixed via the set screws 511. The joint 521 may also be tightened to restrict its movement to further fix the position of the C-bracket 250 with respect to the ankle.

Figure 6:
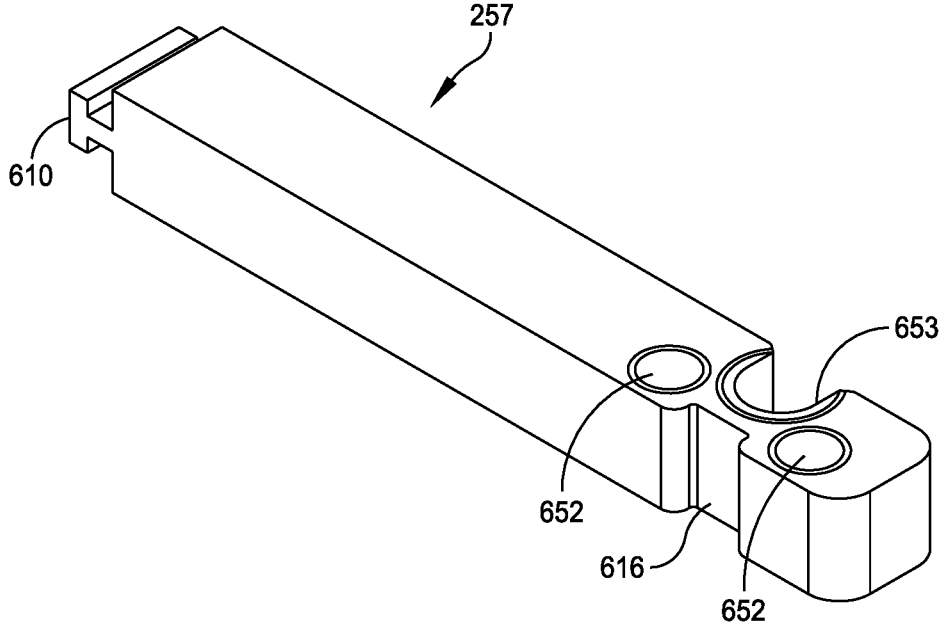
FIG. 6 is an illustration of the distal alignment arm in accordance with embodiments of the disclosed subject matter.

FIG. 6 is an illustration of the distal alignment arm 257. The distal arm 257 extends from cross member 253 and is attached via a key 610 which corresponds to a complementary channel in the cross member 253. The distal arm 257, unlike the proximal alignment arm 256, remains attached at same position irrespective use with the left or right ankle. The anterior mounting block 260 is positioned under the distal alignment arm 257, such that the positioning aids 309 (shown as dowels but may encompass other geometries) are received within positioning recesses 652 (shown as holes) of the distal alignment arm 257. The anterior mounting block 260 is held into position with respect to the distal arm 257 via the compression screw 310 within cooperating slot 653. Opposite the cooperating slot 653 is a recess 616 to allow clearance to compression screw 312 (see FIG. 3). The distal alignment arm 257 forms a rigid connection between the anterior mounting block 260 and the C-bracket 250. The distal alignment arm 257 and the proximal alignment arm 256 via the pins 708, 552 (along with the anterior mounting block 260 and registration reference housing 270) rigidly fix the position of the tibia 111 with respect to the C-bracket 250. Both the distal alignment arm 257 and proximal alignment arm 256 may be constructed of Radel®, Aluminum, plastic, carbon fiber composite, stainless steel or other appropriate material considering the functions and use environment of the alignment arms and C-Bracket in general.

Figure 7B:
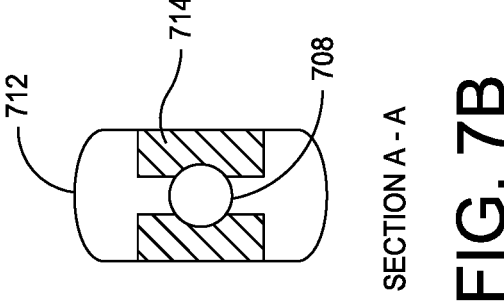
FIGS. 7A and 7B illustrate a registration reference housing, registration pins and sleeves in accordance with embodiments of the disclosed subject matter.
Figure 7A:
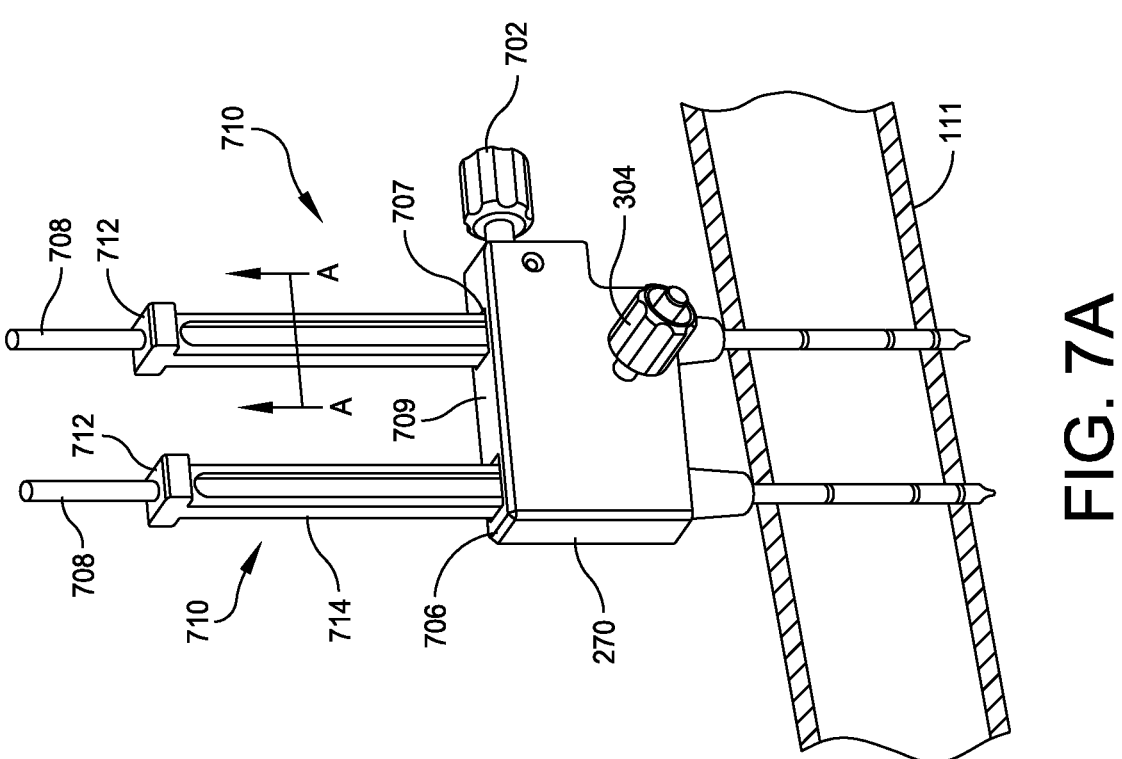
Figure 8:
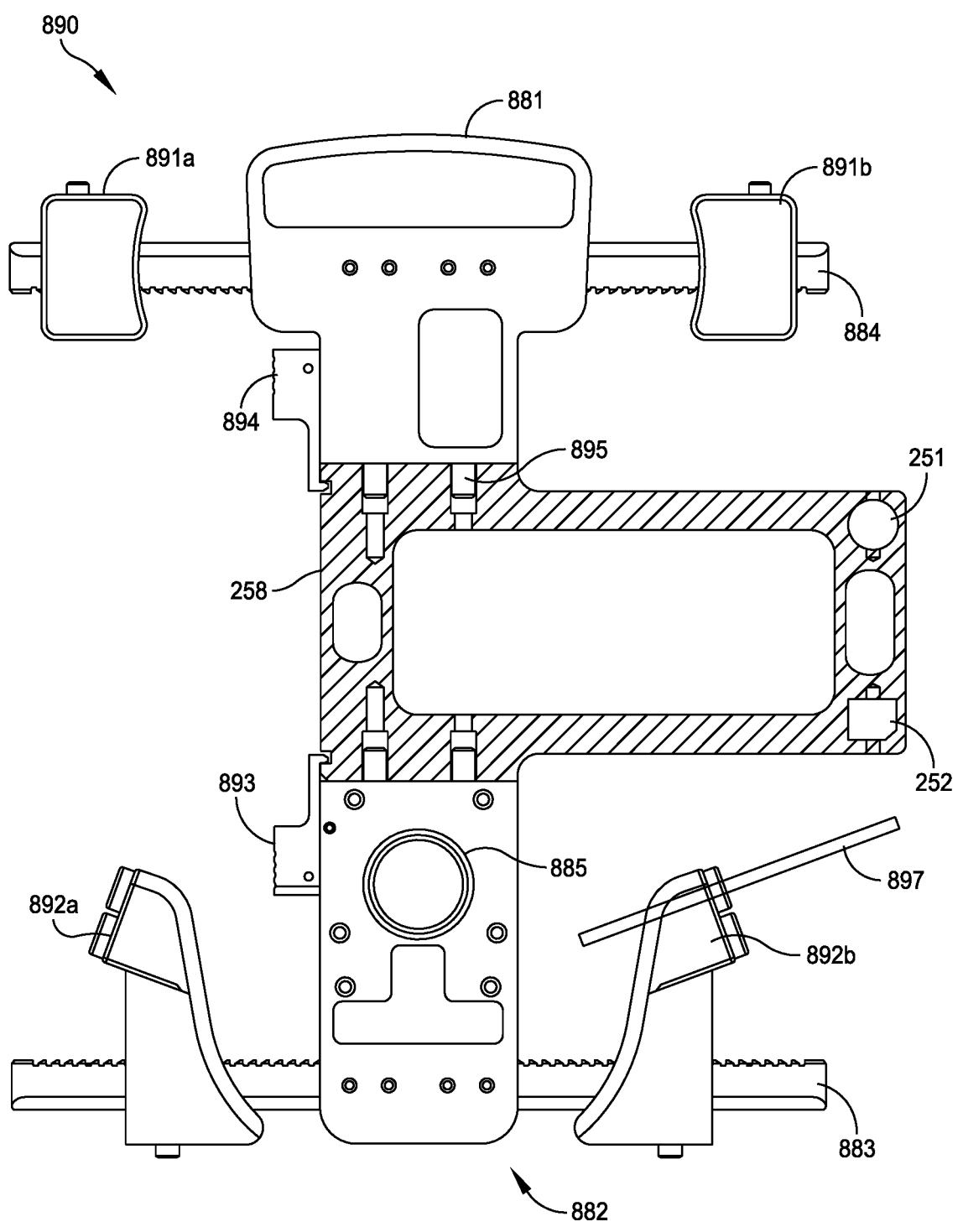
FIG. 8 is an illustration of an assembled foot brace in accordance with embodiments of the disclosed subject matter.

Turning to FIGS. 7A and 7B which illustrate a registration reference housing 270, registration pins 708 and sleeves 710. The registration reference housing 270 is positioned within and adjustable with respect to the anterior mounting block 260 as shown in FIG. 3. The registration reference housing 270 attaches the pins 708 to the anterior mounting block 260. The registration reference housing 270 defines preferably two openings to receive the pins 708 and their respective sleeves 710. The pins 708 are fixed within the tibia 111, preferably passing through the bone to provide rigid support. As shown in FIG. 7B, the sleeves 710 encompass the pins 708 to provide a substantially square cross section 714, that corresponds to the shape of the openings 707 and 706 in the registration reference housing 270, other geometric cross sections are also envisioned, such as diamonds, hexagon, n-gons, stars, cruciform etc. that allow frictional fixation of the pins with the housing. The sleeves 710 allow the registration reference housing 270 to be adjustably positioned vertically along the sleeves 710. The vertical position of the registration reference housing 270 is fixed via set screw 702, which compresses the sleeves 710, and the spacer 709 within the housing 270 to fix its position, with respect to the pins 708. Multiple spacers may be used to properly align and fix the sleeves within the housing. Preferably, two coplanar pins 708 are provided in the tibia 111, such that once fixed within the housing 270, the anterior mounting block 260 may be adjustably attached to the tibia 111 via the pins 708 of the registration reference 270. The longitudinal degree of freedom is fixed as discussed above via set screw 304 and the lateral degree of freedom is fixed as shown in FIG. 3 and FIGS. 10A-B respectively.

The sleeves 710 are tapered at one end such that the may be pushed into contact with the surface of the tibia 111 and are capped at the other end with a head 712 which assists in pushing the sleeves 710 into contact with the tibia 111. As noted previously, these registration pins 708 register (position) the anterior mounting block 260 with respect to the joint shaping step preformed prior to the attachment of the C-bracket 250.

Figure 9:
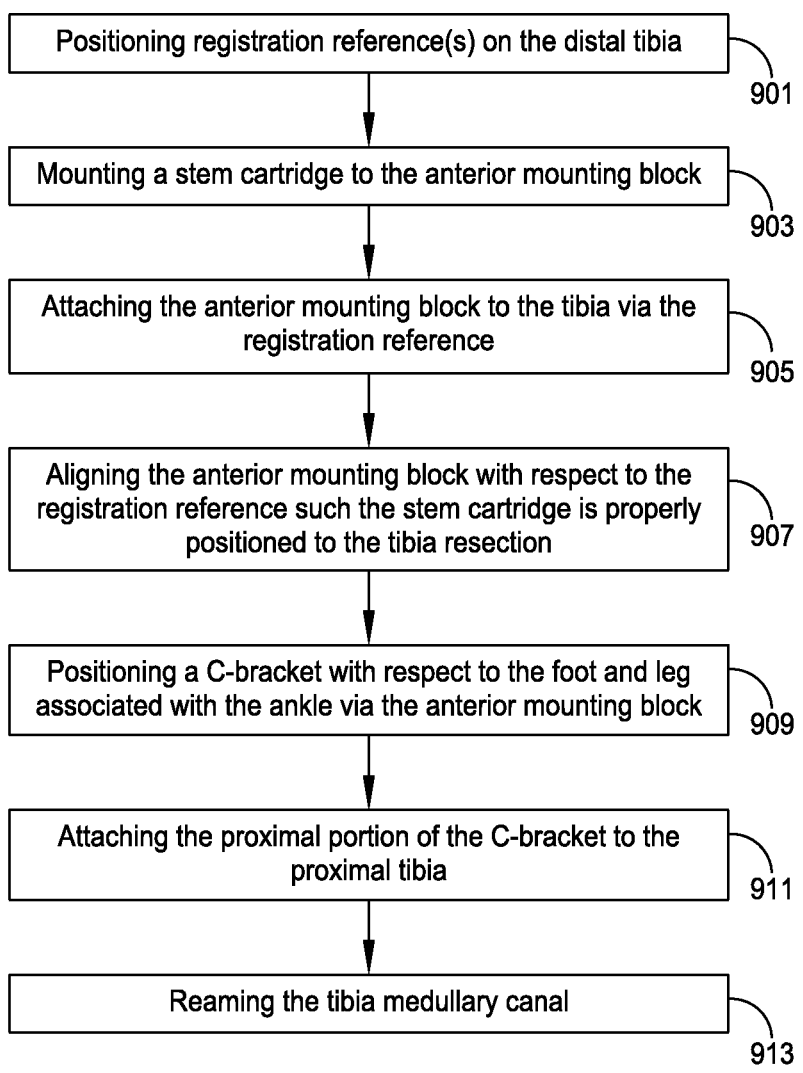
FIG. 9 is a flow chart of a method inter-medullary canal reaming in accordance with embodiments of the disclosed subject matter; and, FIGS. 10A and 10B illustrate lateral adjustments for positioning the stem cartridge with respect to the tibia resection according to embodiments of the disclosed subject matter.

FIG. 9 is a flow chart 900 of a method for inter medullary canal reaming using the described C-Bracket and associated components previously described. A registration reference is positioned on the distal tibia as shown in Block 901. The registration reference(s) e.g. Steinmann pins 708, K-wires, rods, etc., are fixed in the tibia 111. The registration references are preferably placed prior to the joint space shaping and serve to fix the resection guide to the tibia 111, or in some scenarios subsequent to the joint space shaping but positioned with reference to the resultant resection. For example, a resection guide may be positioned on the distal tibia via the registration reference where the resection of the distal tibia is accomplished using the resection guide. In one embodiment the registration reference includes two coplanar pins inserted into the distal tibia, the two co-planar pins 708 extending from the distal tibia and are enveloped by a registration housing 270.

A stem cartridge is mounted to the anterior mounting block 260 as shown in Block 903. A channel (groove) 308 in the anterior mounting block 260 receives a cooperating track (tongue) of the stem cartridge 280.

The anterior mounting block is attached to the registration reference as shown in Block 905. The anterior mounting block 260 is placed over the pins 708 of the registration reference such that the pins 708 pass through the openings 706 and 707 of the registration reference housing 270. The sleeves 710 are then pushed over the pins 708 through the openings 706 and 708 until the tips reach the surface of the tibia 111. The registration reference housing and sleeves may be positioned over the pins concurrent with the placement of the anterior mounting block 260 on the tibia 111, or prior to the placement.

The vertical position of the anterior mounting block 260 with respect to the pins 708 is established and corresponds with the selection of the stem cartridge for the selected tibia implant and the positioning of the stem cartridge within the resection and the set screw 702 fixes the reference housing 270 at that position to the pins 708. The longitudinal positioning within the AP plane and the lateral positioning of the stem cartridge may also be fine-tuned via adjustment of the registration reference housing 270 within cavity 302 and fixed via set screw 304. Alternatively, the anterior mounting block 260 may be positioned on the tibia over the registration reference 270 and then the stem cartridge 280 may be attached to the anterior mounting block 260 and adjusted with respect to the tibia resection.

The stem cartridge 280 and anterior mounting block 260 positioned on the tibia 111 via the registration reference are adjusted, such that the stem cartridge 280 is in contact with the tibia 111 at the resection. The position of the stem cartridge and anterior mounting block 260 may be adjusted with respect to registration reference housing 270 to ensure the stem cartridge 280 engages and properly aligns with the resection, as shown in Block 907. The attachment of the stem cartridge 280 may be performed prior to or after attachment of the anterior mounting block to the tibia 111 via the registration reference 270.

Subsequent the attachment and alignment of the anterior mounting block 260 on the tibia 111, the C-bracket 250 is positioned with respect to the foot and leg associated with the ankle via the anterior mounting block 260 as shown in Block 909. The C-bracket as described previously is lowered down over the anterior mounting block 260 and attaches to the anterior mounting block 260 via the distal alignment arm 257 and is fixed in position via a swiveling compression screw 310, by rotating the compression screw 310 up and over the distal alignment arm 257 and tightening the screw 310.

The proximal portion of the C-bracket 250 is attached to the tibia 111 as shown in Block 911. The attachment is via an alignment pin positioned within and fixed to a proximal alignment arm 256 extending from the C-bracket 250. The proximal cross member 254 is positioned on the rails 251 and 252 and the proximal alignment arm 256 is positioned to receive the pin(s) 552 as shown in FIG. 5 and the set screws 511 fix the pin(s) 552 to the proximal arm 256 thus further attaching the C-bracket 250 to the tibia 111.

Additionally, a foot pad 890 including fore foot pads and heel cups may be used to secure and position the C-bracket 250 to the foot and as discussed above, additional pins may be inserted through the heel cups and secured in the calcaneus bone. For example, with the foot in slight dorsiflexion, the distal alignment arm 257 may be held in place, the distal end of the C-Bracket 250 may be slid close to the bottom of the foot, such that a slight gap is left between the heel and the bushing attachment 885 to facilitate it's removal, then lock the position of the C-Bracket by locking the distal cross member 253 to the ratcheted rail (251 or 252). Preferably the slide release/lock apparatus on the cross members are biased in the locked position.

The tibia medullary canal is then reamed as shown in Block 913. A bushing is attached to the bushing attachment 885, which guides the shaft of the drill into the tibia medullary canal. The shaft of the Reamer drive is placed through the bushing, calcaneus and talus and into the resected joint space. Thru the stem cartridge 280 the reamer tip is attached to the shaft and the reamer is advanced into the tibia medullary canal. The tibia medullary canal is reamed to the depth of the tibia stem construct determined by the preoperative plan. The reamer tip may then be removed through the stem cartridge 280 in the joint space and the reamer shaft removed from the bushing guide. The C-bracket 250 being fixed with respect to the tibia 111 along with the bones of the foot and ankle and the bushing attachment 885 aiding the precision of the reaming.

Prior to reaming, an alignment rod may be attached via a bracket to the anterior mounting block 260 by which using a fluoroscope, the reamer trajectory may be confirmed. The reamer or reamer shaft may be advanced incrementally and its position and orientation verified via the alignment rod as it is advanced.

When properly aligned, the C-Bracket 250 will place the drill anterior and medial to the posterior facet of the subtalar joint. Under a lateral fluoroscopic image, the drill shaft should appear to be inline or parallel with the lateral process of the talus.

An aspect of the disclosed subject matter is that it may be used on the foot for any procedure, as well as other body parts. The C-Bracket 250 is symmetrically designed to be used on either the medial or lateral side of the foot based on surgeon preference, as well as for either the left or right foot.

Although the methods described above are with reference to the illustrated flowchart, it will be appreciated that many other ways of performing the acts associated with the methods can be used. For example, the order of some operations may be changed, and some of the operations described may be optional.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A system for ankle replacement, comprising:
a C-bracket and
a registration reference;
the C-bracket comprising;
two parallel rails extending longitudinally and connected at a proximal end by a proximal end brace and at a distal end by a distal end brace, each of the proximal and distal end braces extending perpendicular between the two parallel rails;
a first cross member extending between the two parallel rails, the cross member fixable to a plurality of longitudinal positions along the two parallel rails,
a second cross member extending between the two parallel rails, the second cross member also fixable to a second plurality of longitudinal positions along the two parallel rails;
a distal alignment arm extending from the first cross member, perpendicular to both the first cross member and the two parallel rails;
an anterior mounting block connected to the distal alignment arm so as to register the C-bracket to the registration reference;
a proximal alignment arm extending from the second cross member, the proximal alignment arm having a mount for fixing an alignment pin at one of a plurality of orientations;
a foot bracket extending from the distal end of the parallel rails and perpendicular to a plane defined by the parallel rails; and,
the registration reference comprising: one or more pins; one or more pin sleeves engaging the one or more pins; and,
a registration housing receiving the one or more pin sleeves and adjustable vertically with the one or more pin sleeves.

2. The system of claim 1, further comprising a stem cartridge.

3. The system of claim 1, wherein the c-bracket is made from aluminum, Polyphenylsulfone or stainless steel.

4. The system of claim 1 wherein the proximal alignment arm is configured to attach to respective ends of the second cross member.

5. The system of claim 1, further comprising an alignment rod connected via a bracket to the anterior mounting block.

6. A system for ankle replacement, comprising:

a C-bracket and a registration reference wherein the registration reference comprises a pin and a registration housing, the registration housing fixedly adjustable along an axis of the pin;

the C-bracket comprising;

two parallel rails extending longitudinally and connected at a proximal end by a proximal end brace and at a distal end by a distal end brace, each of the proximal and distal end braces extending perpendicular between the two parallel rails:

a first cross member extending between the two parallel rails, the cross member fixable to a plurality of longitudinal positions along the two parallel rails, a second cross member extending between the two parallel rails, the second cross member also fixable to a second plurality of longitudinal positions along the two parallel rails;

a distal alignment arm extending from the first cross member, perpendicular to both the first cross member and the two parallel rails;

an anterior mounting block connected to the distal alignment arm so as to register the C-bracket to the registration reference;

a proximal alignment arm extending from the second cross member, the proximal alignment arm having a mount for fixing an alignment pin at one of a plurality of orientations;

a foot bracket extending from the distal end of the parallel rails and perpendicular to a plane defined by the parallel rails; and, the registration reference comprising:

one or more pins;

one or more pin sleeves engaging the one or more pins; and, a registration housing receiving the one or more pin sleeves and adjustable vertically with the one or more pin sleeves.

7. The system of claim 6, wherein the registration housing is configured to receive a second pin.

8. The system of claim 6, wherein the anterior mounting block receives the registration housing within a longitudinally cavity extending through the anterior mounting block parallel to the A-P plane.

9. The system of claim 8, wherein the registration housing is adjustable with respect to the anterior mounting block in the longitudinal, lateral and vertical directions.

10. The system of claim 9 wherein the registration housing is retained in the longitudinal direction with respect to the anterior mounting block via a set screw.

11. The system of claim 9, wherein the registration housing is retained in the lateral direction with respect to the anterior mounting block via shims, wedges, set screws or worm screws.

* * * * *